United States Patent
Ramadan

(12) 
(10) Patent No.: US 6,224,546 B1
(45) Date of Patent: May 1, 2001

(54) STABILIZED CEPHALIC MEDICAL APPARATUS, AND METHOD OF USING SAME

(75) Inventor: Ahmad Yaser Ramadan, Cairo (EG)

(73) Assignees: Kalil Jiraki, Detroit; Mohamed El-Naggar, Dearborn, both of MI (US); part interest to each ( * ) Notice: Subject to any disclaimer, the term of this patent is extended or adjusted under 35 U.S.C. 154(b) by 0 days.

(21) Appl. No.: 09/312,081

(22) Filed: May 15, 1999

(30) Foreign Application Priority Data

May 17, 1998 (EG) .................................................. 50533-98

(51) Int. Cl.[7] .................................................. A61B 17/02
(52) U.S. Cl. .......................... 600/235; 600/228; 600/229
(58) Field of Search .................................... 600/227, 228, 600/229, 230, 235, 236, 237, 246, 245

(56) References Cited

U.S. PATENT DOCUMENTS

| | | | |
|---|---|---|---|
| 369,114 | * 8/1887 | Knapp | 600/229 |
| 432,614 | * 2/1890 | Hendrick | 600/227 |
| 605,715 | * 6/1898 | Hohmann | 600/227 |
| 837,996 | * 12/1906 | Youngman | 600/227 |
| 1,230,873 | * 6/1917 | Crossley | 600/228 |
| 1,237,121 | * 8/1917 | Soffa | 600/227 |
| 1,375,445 | * 4/1921 | Crossley | 600/227 |
| 1,465,259 | * 8/1923 | Friedman | 600/227 |
| 1,710,377 | * 4/1929 | Niflot | 600/230 |
| 3,976,054 | 8/1976 | Evans . | |
| 4,254,763 | * 3/1981 | McCready et al. | 600/228 |
| 4,576,168 | 3/1986 | Jalowayski . | |
| 4,971,037 | * 11/1990 | Pelta | 600/230 |
| 5,054,906 | * 10/1991 | Lyons, Jr. | 600/245 |
| 5,529,358 | * 6/1996 | Dinkler et al. | 600/229 |
| 5,569,300 | * 10/1996 | Redmon | 600/245 |
| 5,609,565 | * 3/1997 | Nakamura | 600/228 |
| 5,772,582 | 6/1998 | Huttner et al. . | |
| 5,931,777 | * 8/1999 | Sava | 600/235 |

OTHER PUBLICATIONS

Micro–France® Endo–Nasal Micro Surgery product list.

* cited by examiner

Primary Examiner—Paul J. Hirsch
(74) Attorney, Agent, or Firm—Carrier, Blackman & Associates, P.C.; William D. Blackman; Joseph P. Carrier

(57) ABSTRACT

A stabilized cephalic medical apparatus includes an annular band for placement around a patient's head, and a pivotally adjustable bridge member for holding and supporting a medical instrument. The bridge member according to the invention is attachable to the annular band, and is preferably removable therefrom for cleaning and sterilization thereof. The bridge member is preferred to include a mounting member for supporting a medical instrument thereon, and a connector for connecting the mounting member to the annular band. The apparatus may further include a medical instrument attachable to the bridge member. The design of the apparatus according to the invention allows a medical instrument, such as a nasal speculum or retractor, to be operatively attached to, and to move concurrently with the patient. Attachment of the medical instrument to a patient tends to minimize or eliminate complications arising from movement of a patient's head with respect to a fixed in place speculum, retractor, or other medical instrument. A method of using the apparatus in connection with a medical instrument is also described.

14 Claims, 4 Drawing Sheets

STABILIZED CEPHALIC MEDICAL APPARATUS, AND METHOD OF USING SAME

CROSS-REFERENCE TO RELATED APPLICATIONS

The present application claims foreign priority, under 35 U.S.C. section 119, of Egyptian patent application Ser. No. 50533-98, filed May 17, 1998. The disclosure of Egyptian patent application Ser. No. 50533-98 is incorporated herein by reference.

BACKGROUND OF THE INVENTION

1. Field of the Invention

The present invention relates to a speculum apparatus which is adapted for use by ear, nose and throat (ENT) medical specialists for dilating an aperture in a patient's head, such as, e.g., a nasal opening. More particularly, the present invention relates to a stabilized cephalic speculum apparatus, or similar stabilized medical instrument, which is attachable to a patient's head for concurrent movement therewith.

2. Description of the Background Art

Many types of medical specula, for a physician's use in dialating an aperture in a patient's body in a medical examination, are known and commercially available. Examples of some known designs for manually operated nasal specula are disclosed in U.S. Pat. Nos. 4,576,168 and 5,772,582.

A nasal speculum attached to a flexibly movable articulated arm, in which an end of the arm opposite the speculum is clampably attachable to an examining or operating table, is commercially available and is sold by the French company Micro-France. Other types of medical tools are available for facilitating medical examination and surgical work on a patient's ear canal.

Unfortunately, a problem exists with the known devices in that during a medical procedure such as, e.g., nasal surgery, a doctor may wish to adjust the position of a patient's head, or the patient may move their head somewhat. When this type of head movement occurs, if the medical instrument remains fixed in place while the head moves, problems may result. At a minimum, after moving a patient's head, time consuming readjustment of the apparatus is required. If the doctor is using a hand-held medical instrument such as a nasal retractor or speculum, this makes it difficult to use the hands for other tasks. Where an assistant is brought in to hold the speculum, space around the patient can become cluttered and obstructed.

While the known cephalic specula and related instruments are useful for their intended purposes, a need still exists in the art for a medical apparatus which is painlessly attachable to a patient, to allow movement of an attached medical instrument concurrently with movement of a patient's head.

SUMMARY OF THE INVENTION

The present invention provides a stabilized cephalic medical apparatus including an annular band for placement around a patient's head, and a pivotally adjustable holder mechanism, which is attachable to the annular band, for holding and supporting a medical instrument. The holder mechanism according to the invention is preferably removable from the annular band, for cleaning and sterilization thereof.

The design of the apparatus according to the invention allows a medical instrument, such as for example, a nasal speculum or retractor, to move concurrently with movement of a patient's head, to minimize or eliminate complications which could otherwise result from movement of a patient's head with respect to a fixed-in-place medical instrument.

Accordingly, it is an object of the present invention to provide a method and apparatus for supportively holding a medical instrument in operatively connected relation to a patient's head, while freeing a doctor's hands for surgical or other tasks.

It is another object of the present invention to provide an apparatus of the type described which is adapted to be usable with a variety of cephalic medical instruments.

For a more complete understanding of the present invention, the reader is referred to the following detailed description section, which should be read in conjunction with the accompanying drawings. Throughout the following detailed description and in the drawings, like numbers refer to like parts.

DETAILED DESCRIPTION OF THE PRESENTLY PREFERRED EMBODIMENTS

I. Overview

Figure 1:
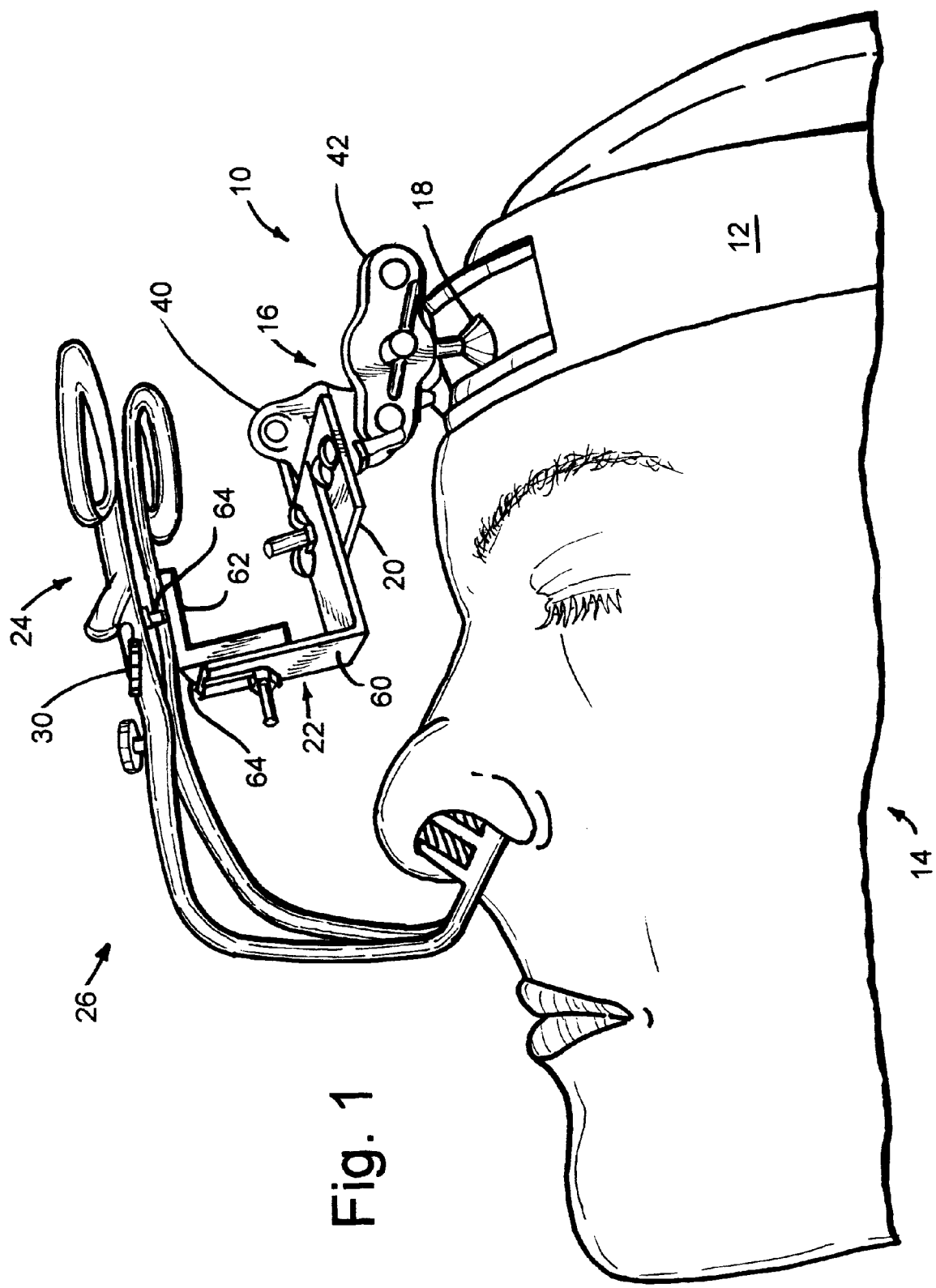
FIG. 1 is an environmental perspective view of a stabilized cephalic medical apparatus in accordance with a first embodiment of the present invention, shown emplaced on a patient's head and supporting a nasal retractor.
Figure 2:
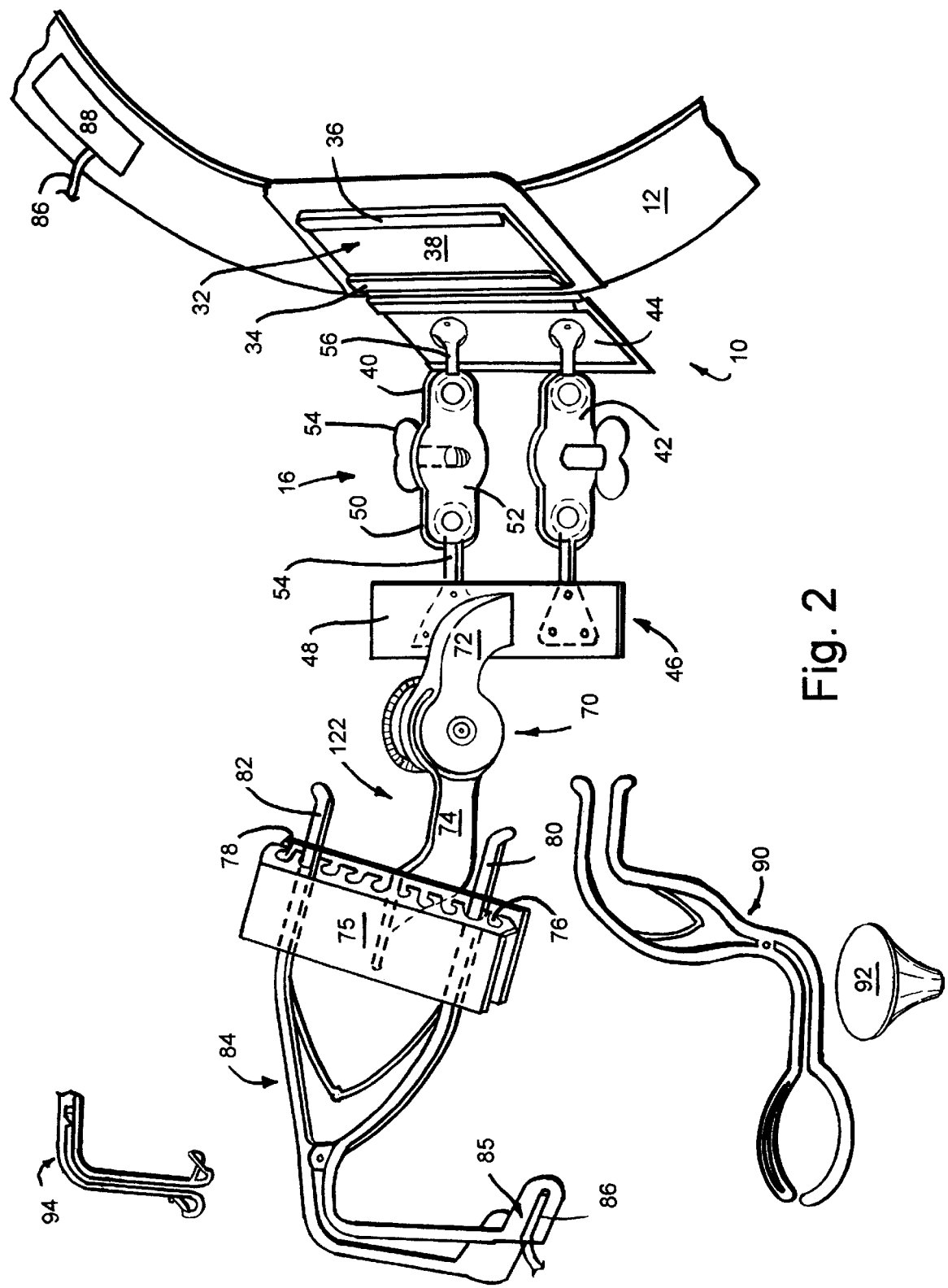
FIG. 2 is an exploded perspective view of a second embodiment of the invention, shown supporting a nasal speculum.

Referring now to FIGS. 1–2 of the drawings, a stabilized cephalic medical apparatus, in accordance with the invention, is shown generally at 10. The apparatus 10 includes an adjustable annular band 12 which is constructed and arranged to be worn by, and accordingly to be operatively and removably attached to a patient's head 14.

A bridge member 16 is provided for connecting to the annular band. A first end 18 of the bridge member is attachable to the annular band 12, and a second end 20 thereof is attached to an intermediate support member 22.

The intermediate support member 22 has a medical instrument 24 adjustably attached thereto. In the illustration of FIG. 1, the particular medical instrument shown is a retractor 30, which has been particularly configured to be used with the apparatus 10 hereof. Other medical instruments may alternately be used. Each of the above-mentioned components will be described in further detail below.

The annular band 12 and the bridge member 16 shown in FIG. 2 are substantially identical to the same components in the embodiment of FIG. 1. The intermediate support member 122 in the embodiment of FIG. 2 is different from the intermediate support member 22 of FIG. 1.

The entire assembly is generically designated herein by the reference number 26, and the assembly includes the annular band 12, the bridge member 16, the intermediate support member 22 or 122 and a suitable medical instrument 24.

II. The Annular Band

The annular band 12 is preferably made to be adjustable to be usable with different head sizes. Once adjusted, however, the band size should remain constant unless readjusted, because it is required to be a stable support member for a medical instrument 24.

The band 12 is most preferably made of a strong, flexible plastic material so as to be relatively comfortable for the patient 14.

The bridge member 16 may be permanently affixed to the band 12. Alternatively, and optionally, the annular band 12 may have a supportive backing plate 32 affixed thereto by rivets or other conventional fastening means (not shown). The backing plate 32, where used, is preferably made of metal such as aluminum or steel. In the embodiment of FIG. 2, the backing plate 32 includes a pair of opposed side rails 34, 36 which are slightly spaced outwardly away from the base portion 38 thereof.

Another optional feature that may be included as a part of the annular band is a light generating device 88, which may include a battery pack.

III. The Bridge Member

The bridge member 16 is provided for interconnecting an intermediate support member 22 or 122 to the annular band 12. The bridge member 16 is preferably made of metal or a strong, durable plastic. Preferably, but not necessarily, the bridge member includes a base plate 44 which is made to be slidably insertable in the backing plate 32 of the annular band, behind the side rails 34, 36 thereof.

The bridge member 16 includes at least one, and preferably two pivotally adjustable connectors 40, 42 extending from the base plate 44 to a mounting member 46.

As shown by the illustrative connector 40 of FIG. 2, in this embodiment, each of the pivotally adjustable connectors 40, 42 includes a pair of opposed apertured plates 50, 52 interconnected by a shouldered bolt 54. The innermost plate 52 has a central threaded bore formed therein, and tightening the shouldered bolt 54 against the outer plate 50 clamps the plates 50, 52 together and fixes the position thereof with respect to a pair of post-mounted spherical connectors, the spherical heads of which are trapped between the plates 50, 52 to define a type of double-ended ball and socket joint.

In the embodiment of FIGS. 1–2, the mounting member 46 takes the form of a generally flat plate 48. The mounting member 46 may be made in any convenient shape, although it has been found that the flat plate 48 is workable as the mounting member. The mounting member 46 is preferred to have a hole formed centrally therein to receive a fastener for use in attaching an intermediate support member 22 or 122 thereto.

IV. The Intermediate Support Member

Referring now to FIG. 1, a first type of intermediate support member 22 according to the present invention includes opposed first and second L-shaped brackets 60, 62 which are interconnected by conventional fasteners. The first L-shaped bracket 60, shown on the bottom in the Figure, has a slot 64 formed therein to allow relative positioning and spacing of the brackets 60, 62 with respect to one another. The second, or upper L-shaped bracket 62 has a central hole formed in the inverted base thereof, and the medical instrument 24 is mounted thereon, using a tubular spacer 64 to space the instrument upwardly away from the second bracket.

FIG. 2 shows an alternative type of intermediate support member 122 which is usable in the practice of the present invention. The intermediate support member 122, in this embodiment, includes a two-piece pivotally articulated connector arm 70 including a first segment 72 which is attached to the mounting member 46 in conventional fashion, and a second segment 74 pivotally and adjustably connected to the first segment. The connection between the first and second segments 72, 74 is made so that it may be loosened for adjustment of the relative positions thereof, and may then be tightened to hold a preferred orientation of the segments relative to one another. Those skilled in the relevant art will realize that appropriate hardware, such as the shouldered bolt 54 is readily available for making this type of connection.

In the embodiment of FIG. 2, the intermediate support member 122 also includes a substantially L-shaped spacer rack 75 which is glued, welded or otherwise affixed in conventional fashion to the second segment 74 of the two-piece pivotally articulated connector arm 70. The spacer rack 75 has a plurality of opposed slots, such as that shown at 76, 78 formed therein for receiving opposed arms 80, 82 of a spring-loaded medical instrument, such as the nasal speculum 84 shown in the rack.

Optionally, the medical instrument used in connection with the invention, as illustrated by the nasal speculum 84 held by the spacer rack 75, may also carry an attached light source 85 such as a fiber-optic cable 86. Where used, the light source 85 is connected to a light generating means 88, which may be attached to the annular band 12. An alternative light source 85 may be a conventional electric bulb, wiring and battery arrangement.

While the spacer rack 75 may accommodate any number of spring-loaded or other medical instruments therein, the apparatus 10 hereof is particularly usable with the medical instruments discussed herein, as well as with a holder 90 for an ear speculum 92 or with a retractor 94 of the type for use with both alae nasi (both nasal fossae) during rhinoplasty.

ALTERNATE EMBODIMENT OF THE APPARATUS

Figure 3:
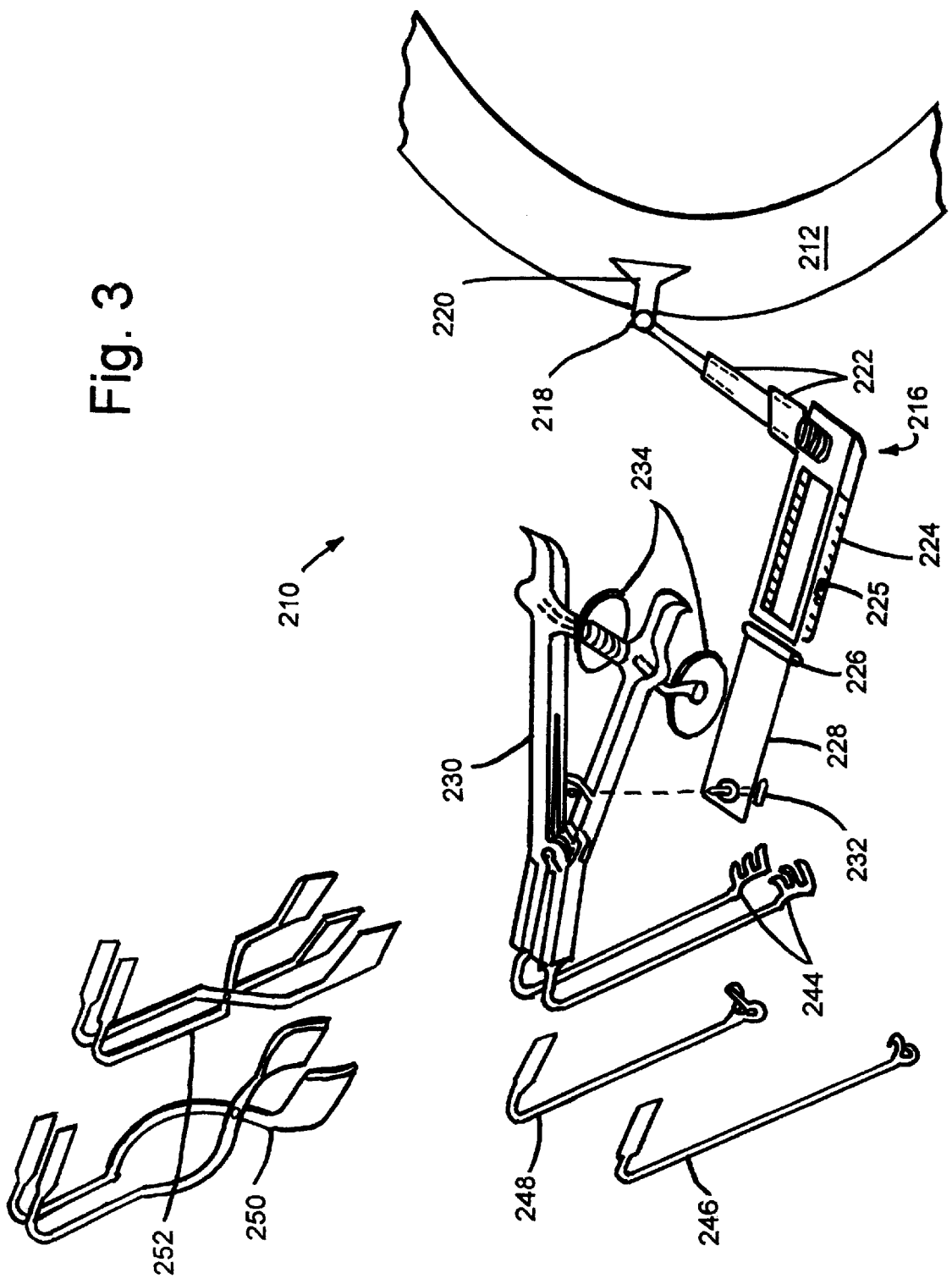
FIG. 3 is an exploded perspective view of a third embodiment of the invention.

Referring now to FIG. 3, an alternate embodiment of a stabilized cephalic medical apparatus according to the invention is shown at 210. The apparatus 210 includes an annular band 212, which is preferably made adjustable to fit different head sizes. The annular band 212 is substantially identical to the annular band 12 as previously described.

The apparatus 210 further includes a bridge member 216 which is attached to the annular band 212. The bridge member 216 includes a pivotally adjustable connection 218, which adjustably connects a base member 220 thereof to an extendable member 222, which includes a nested series of disengagably lockable telescoping sleeves.

The outermost sleeve of the extendable member 222 is affixed to a back plate 224, which includes a plurality of indentations 225 formed thereon to receive projections of an integral cylinder 226 which is part of a sliding plate 228.

Figure 4:
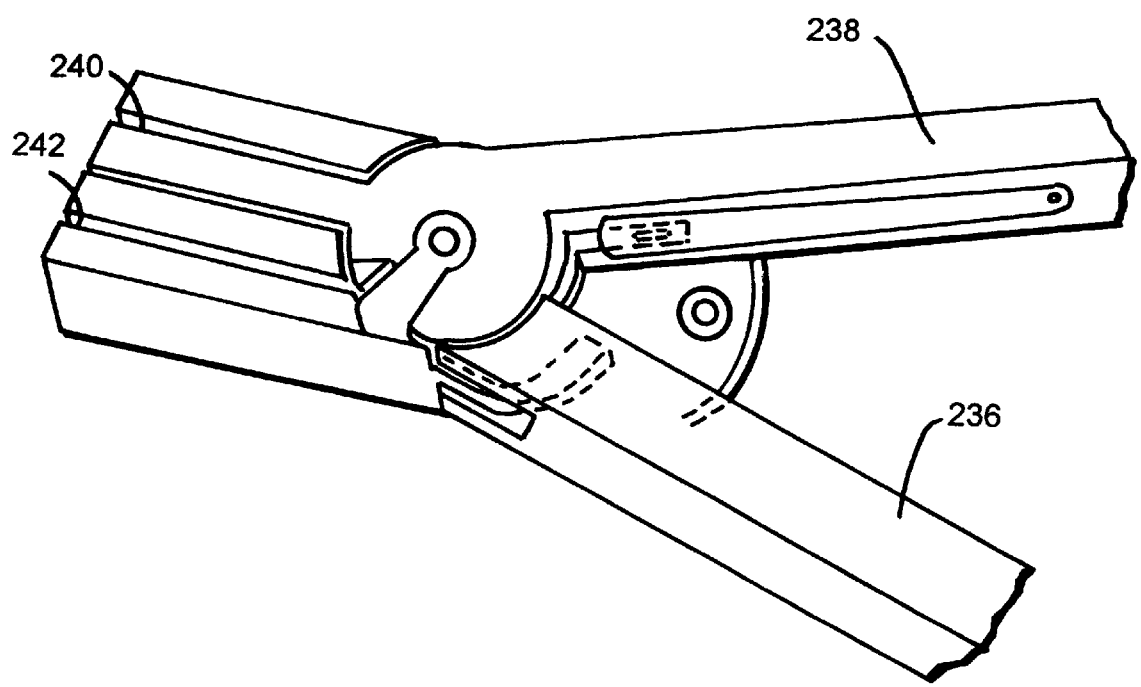
FIG. 4 is a detail view of a self-retaining forceps which is a part of the embodiment of FIG. 3.

A medical instrument, such as, e.g., a self-retaining forceps 230 is affixable to the sliding plate 228, using conventional threaded fasteners 232. The self-retaining forceps 230 may have one or more mirrors 234 attached thereto, and includes a pair of pivotally connected arms 236, 238 (FIG. 4) which are made with open slots 240, 242 formed in the respective ends thereof, to receive particular tool inserts therein as will be subsequently described.

One type of tool insert which may be used with the self-retaining forceps 230 is a pair of opposed retractor arms 244. Other usable inserts include horizonally configured retractors 246, alae nasi retractors 248, and various types of specula such as those shown at 250 and 252. These inserts are shown and described herein as illustrations, and this is not intended to be an exclusive list of possible inserts which may be used.

BENEFITS OF THE APPARATUS

The apparatus 10 according to the invention allows a surgeon to use both hands during patient examination, or during surgery for Submucous resection of the nasal septum (S.M.R.);

Septorhinoplasty;

Microscopic sinus or otic surgery;

Polypectomy;

Myringtomy and grommet insertion; or

Stapedectomy, among other useful procedures.

Use of the apparatus 10 or 210 according to the invention allows the patient's head to be re-positioned without requiring readjustment of the apparatus, since it moves with the head. The multiple pivoting connections allow for highly flexible adjustment of the apparatus to suit the contours of a particular patient, and the needs of the procedure.

When using the assembly 26 according to the invention, the following method is recommended. The method may be varied, and further steps may be added or deleted as appropriate, according to the medical circumstances. First, a towel or other cloth is placed over the head of a patient 14. Then, the annular band 12 or 212 is adjusted to the appropriate size for the patient and is placed around the patient's head. The orientation of the component parts of the assembly 26 is then adjusted, as needed, to fit the particular patient and procedure. All connections are then tightened to fix the orientation of the medical instrument 24 being used.

Then, the proper and appropriate medical procedure is carried out, whether it is an examination, a surgical procedure, or another procedure.

The sliding connection of the base plate 44 in the backing plate 38, where used, allows for easy removal of component parts of the assembly 26 from the annular band 12 or 112, for cleaning and/or sterilization thereof. If towels are used to cover the patient's head below the annular band 12, then there will be no need to re-sterilize the band.

The apparatus 10 or 210 hereof is expected to be relatively inexpensive to manufacture, allowing for affordable pricing thereof, so that virtually every E.N.T. surgeon can afford to own one.

Although the present invention has been described herein with respect to several preferred embodiments thereof, the foregoing description is intended to be illustrative, and not restrictive. Those skilled in the art will realize that many modifications of the preferred embodiments could be made which would be operable. All such modifications which are within the scope of the claims are intended to be within the scope and spirit of the present invention.

I claim:

1. An apparatus for supportively holding a cephalic medical instrument, comprising:
    an annular band for contacting placement around a patient's head;
    a backing plate attached to the annular band for receiving a bridge member thereon;
    a bridge member which is attachable to the annular band, the bridge member comprising:
        a mounting member for operatively attaching to a medical instrument, said mounting member comprising
            pivotably adjustable connection means for connecting the mounting member to the annular band, said adjustable connection means comprising a base plate which is slidably attachable to the backing plate on the annular band.

2. The apparatus of claim 1, further comprising a medical instrument operatively attached to the bridge member.

3. The apparatus of claim 2, wherein said instrument comprises a nasal speculum.

4. The apparatus of claim 2, wherein said instrument comprises a retractor.

5. The apparatus of claim 2, wherein said instrument comprises a holder for an ear speculum.

6. The apparatus of claim 1, further comprising an intermediate support member for receiving a medical instrument thereon, the intermediate support member being attached to the mounting member.

7. The apparatus of claim 6, wherein the intermediate support member comprises a spacer rack operatively attached to the mounting member, said spacer rack having a plurality of opposed slots formed therein for receiving opposed arms of a medical instrument therein.

8. The apparatus of claim 1, wherein said backing plate comprises a base portion and a pair of opposed side rails disposed on opposite sides of the base portion and spaced away therefrom; and wherein the bridge member is slidably attachable to the backing plate on the annular band by sliding the bridge member base plate between the base portion and the side rails of the backing plate.

9. The apparatus of claim 1, further comprising means for generating light.

10. The apparatus of claim 1, wherein the mounting member further comprises a spacer rack having a plurality of opposed slots formed therein, for selectively receiving opposed arms of a medical instrument.

11. An apparatus for supportively holding a cephalic medical instrument, comprising:
    an annular band for placement around a patient's head;
    support means attached to the annular band for holding and supporting a bridge member thereon;
    a bridge member which is engagably attachable to the support member, the bridge member comprising a mounting member for operatively supporting a medical instrument and pivotably adjustable connection means for connecting the mounting member to the support means of the annular band;
    an intermediate support member for receiving a medical instrument thereon, the intermediate support member being attached to the mounting member; and a medical instrument operatively attached to the intermediate support member, said medical instrument comprising a pair of pivotally connected arms, each of said arms having a forward end with an opening formed therein to receive a tool insert.

12. The apparatus of claim 11, further comprising a tool insert for each of said arms.

13. The apparatus of claim 11, wherein the connection means of the bridge member comprises a dual ball and socket mechanism.

14. A method of operatively attaching a medical instrument to a patient's head in preparation for a medical procedure, comprising the steps of:

a) providing the apparatus of claim 1 and attaching a selected medical instrument thereto;

b) adjusting the annular band to an appropriate size for the patient;

c) placing the annular band around the patient's head;

d) adjusting orientation of component parts of the apparatus, as needed, to fit the patient;

e) tightening connections on the apparatus to fix the orientation of the medical instrument.

* * * * *